(12) United States Patent
Prior (10) Patent No.: US 12,193,660 B2
(45) Date of Patent: *Jan. 14, 2025

(54) TRANS-VAGINAL CUFF ANCHOR AND METHOD OF DEPLOYING SAME

(71) Applicant: Covidien LP, Mansfield, MA (US)

(72) Inventor: Scott J. Prior, Branford, CT (US)

(73) Assignee: Covidien LP, Mansfield, MA (US)

( * ) Notice: Subject to any disclaimer, the term of this patent is extended or adjusted under 35 U.S.C. 154(b) by 413 days.

This patent is subject to a terminal disclaimer.

(21) Appl. No.: 17/826,280

(22) Filed: May 27, 2022

(65) Prior Publication Data

US 2022/0280151 A1    Sep. 8, 2022

Related U.S. Application Data

(63) Continuation of application No. 16/396,724, filed on Apr. 28, 2019, now Pat. No. 11,344,292.

(Continued)

(51) Int. Cl.
*A61B 17/04* (2006.01)
*A61B 17/42* (2006.01)
*A61B 17/00* (2006.01)

(52) U.S. Cl.
CPC ...... *A61B 17/0469* (2013.01); *A61B 17/0487* (2013.01); *A61B 17/4241* (2013.01);
(Continued)

(58) Field of Classification Search
CPC ............ A61B 17/1114; A61B 17/0401; A61B 17/0469; A61B 17/29; A61B 2017/00818;
(Continued)

(56) References Cited

U.S. PATENT DOCUMENTS

| 4,597,030 A | 6/1986 | Brody et al. |
| 4,804,240 A | 2/1989 | Mori |

(Continued)

FOREIGN PATENT DOCUMENTS

| CN | 202489982 U | 10/2012 |
| CN | 202920313 U | 5/2013 |

(Continued)

*Primary Examiner* — Ashley L Fishback
*Assistant Examiner* — Chima U Igboko
(74) *Attorney, Agent, or Firm* — Carter, DeLuca & Farrell LLP (57) ABSTRACT

A surgical device for closing a vaginal cuff includes a handle having an elongated shaft and a plurality of needles disposed therein. Each needle includes a suture anchor at a distal end thereof having a suture engaged therewith. An anvil is disposed at a distal end of the elongated shaft. A cutting mechanism is operably associated with the handle and is configured to cut tissue upon actuation thereof. A firing mechanism is operably associated with the handle and is movable between an unactuated position wherein the plurality of needles and suture anchors remain retained within the elongated shaft, an actuated position wherein the plurality of needles and suture anchors deploy from the elongated shaft through the cervical tissue, and a reverted position wherein the plurality of needles retract leaving the plurality of suture anchors and sutures engaged with the cervical tissue for tying off the vaginal cuff.

17 Claims, 9 Drawing Sheets

Related U.S. Application Data (60) Provisional application No. 62/684,794, filed on Jun. 14, 2018.

(52) U.S. Cl.
CPC . *A61B 17/00234* (2013.01); *A61B 2017/0488* (2013.01); *A61B 2017/4225* (2013.01)

(58) Field of Classification Search
CPC .... A61B 2017/0409; A61B 2017/0417; A61B 2017/0464; A61B 2017/0496; A61B 2017/06052; A61B 2017/0647; A61B 2017/1139; A61B 17/0487; A61B 17/4241; A61B 17/00234; A61B 2017/0488; A61B 2017/4225; A61B 34/30; A61B 2017/4216; A61B 17/42; A61B 90/92; A61B 2017/0472
See application file for complete search history.

(56) References Cited

U.S. PATENT DOCUMENTS

| | | | |
|---|---|---|---|
| 5,197,649 A * | 3/1993 | Bessler | A61B 17/115 600/129 |
| 5,209,754 A | 5/1993 | Ahluwalia | |
| 5,394,863 A | 3/1995 | Sanford et al. | |
| 5,451,221 A | 9/1995 | Cho et al. | |
| 5,487,377 A | 1/1996 | Smith et al. | |
| 5,520,698 A | 5/1996 | Koh | |
| 5,643,285 A | 7/1997 | Rowden et al. | |
| 5,840,077 A | 11/1998 | Rowden et al. | |
| 6,029,806 A | 2/2000 | Cerwin | |
| 6,032,673 A | 3/2000 | Savage et al. | |
| 6,129,662 A | 10/2000 | Li et al. | |
| 6,423,075 B1 | 7/2002 | Singh et al. | |
| 6,516,216 B1 | 2/2003 | Fontenot et al. | |
| 8,025,670 B2 | 9/2011 | Sharp et al. | |
| 8,128,622 B2 | 3/2012 | Podhajsky et al. | |
| 8,192,444 B2 | 6/2012 | Dycus | |
| 8,206,357 B2 | 6/2012 | Bettuchi | |
| 8,292,901 B2 | 10/2012 | Auerbach et al. | |
| 8,298,213 B2 | 10/2012 | Singh | |
| 8,323,278 B2 | 12/2012 | Brecheen et al. | |
| 8,453,910 B2 | 6/2013 | Bettuchi et al. | |
| 8,460,289 B2 | 6/2013 | Sartor | |
| 8,528,563 B2 | 9/2013 | Gruber | |
| 8,545,513 B2 | 10/2013 | Blair et al. | |
| 8,603,105 B2 | 12/2013 | Sauer | |
| 8,663,239 B2 | 3/2014 | Hess | |
| 8,696,563 B2 | 4/2014 | Williams et al. | |
| 8,784,410 B2 | 7/2014 | Dunning | |
| 8,939,988 B2 | 1/2015 | Auerbach et al. | |
| 9,011,433 B2 | 4/2015 | Batchelor et al. | |
| 9,022,927 B2 | 5/2015 | Kleyman | |
| 9,033,977 B2 | 5/2015 | Morozov | |
| 9,066,724 B2 | 6/2015 | Jenkins | |
| 9,101,390 B2 | 8/2015 | Singh et al. | |
| 9,144,454 B2 | 9/2015 | Batchelor et al. | |
| 9,392,935 B2 | 7/2016 | Adams et al. | |
| 11,344,292 B2 | 5/2022 | Prior | |
| 2003/0187334 A1 | 10/2003 | Biswas | |
| 2005/0085827 A1 | 4/2005 | G. et al. | |
| 2005/0228405 A1 | 10/2005 | Maruyama et al. | |
| 2006/0271037 A1 | 11/2006 | Maroney et al. | |
| 2006/0291195 A1 | 12/2006 | Horrell et al. | |
| 2007/0203507 A1 | 8/2007 | McLaughlin et al. | |
| 2008/0208210 A1 | 8/2008 | Blair et al. | |
| 2008/0294001 A1 * | 11/2008 | Surti | A61B 17/0057 606/232 |
| 2010/0087707 A1 | 4/2010 | Surti | |
| 2010/0280524 A1 | 11/2010 | Lopez Zepeda | |
| 2011/0130769 A1 | 6/2011 | Boebel et al. | |
| 2011/0190689 A1 | 8/2011 | Bennett et al. | |
| 2011/0257668 A1 | 10/2011 | Surti | |
| 2012/0016185 A1 | 1/2012 | Sherts et al. | |
| 2012/0116416 A1 | 5/2012 | Neff et al. | |
| 2012/0143210 A1 | 6/2012 | Brecheen et al. | |
| 2012/0165826 A1 | 6/2012 | Rhemrev-Pieters | |
| 2012/0283718 A1 | 11/2012 | Cosmescu | |
| 2012/0323079 A1 | 12/2012 | Bakare et al. | |
| 2012/0330324 A1 | 12/2012 | Sauer | |
| 2013/0066328 A1 | 3/2013 | Singh et al. | |
| 2013/0085508 A1 | 4/2013 | Hess | |
| 2013/0110126 A1 | 5/2013 | Mujwid | |
| 2013/0131459 A1 | 5/2013 | Williams et al. | |
| 2014/0012305 A1 | 1/2014 | Horton et al. | |
| 2014/0180282 A1 | 6/2014 | Brecheen et al. | |
| 2014/0303641 A1 | 10/2014 | Boebel et al. | |
| 2014/0358158 A1 | 12/2014 | Einarsson | |
| 2015/0005780 A1 | 1/2015 | Einarsson | |
| 2015/0080905 A1 | 3/2015 | Begemann et al. | |
| 2015/0127016 A1 | 5/2015 | Sauer | |
| 2015/0351621 A1 | 12/2015 | Hill et al. | |
| 2016/0045757 A1 | 2/2016 | Groseth | |
| 2016/0074186 A1 | 3/2016 | Sartor et al. | |
| 2016/0095649 A1 | 4/2016 | Motai et al. | |
| 2016/0100861 A1 | 4/2016 | Parys et al. | |
| 2016/0100862 A1 | 4/2016 | Parys | |
| 2016/0106463 A1 | 4/2016 | Egle et al. | |

FOREIGN PATENT DOCUMENTS

| | | |
|---|---|---|
| CN | 203244440 U | 10/2013 |
| CN | 203303125 U | 11/2013 |
| CN | 204446045 U | 7/2015 |
| CN | 204698659 U | 10/2015 |
| CN | 205072992 U | 3/2016 |
| DE | 102009018521 A1 | 10/2010 |
| EP | 0865760 A1 | 9/1998 |
| EP | 2243437 A1 | 10/2010 |
| EP | 3068323 A1 | 9/2016 |
| WO | 03015643 A2 | 2/2003 |
| WO | 2008136024 A1 | 11/2008 |
| WO | 2011140604 A1 | 11/2011 |
| WO | 2012151622 A1 | 11/2012 |
| WO | 2013090909 A1 | 6/2013 |
| WO | 2015073147 A1 | 5/2015 |
| WO | 2016025132 A1 | 2/2016 |

* cited by examiner

TRANS-VAGINAL CUFF ANCHOR AND METHOD OF DEPLOYING SAME

CROSS REFERENCE TO RELATED APPLICATION

This application is a continuation of U.S. patent application Ser. No. 16/396,724, filed on Apr. 28, 2019, which claims the benefit of and priority to U.S. Provisional Application Ser. No. 62/684,794, filed on Jun. 14, 2018, the entire contents of each of which is hereby incorporated herein by reference.

TECHNICAL FIELD

The present disclosure relates to laparoscopic hysterectomy devices and procedures and, more particularly, to devices and methods for performing a colpotomy and closing of the vaginal cuff.

BACKGROUND

Colpotomy, one of the final steps in a laparoscopic hysterectomy, requires making a circular incision in vaginal tissue to separate the uterus from the vagina. This incision is typically performed with the aid of a uterine manipulator. Once the uterus and the cervix are removed, the vaginal cuff needs to be closed. Traditionally with open hysterectomies, this was less complicated since the surgeon could visualize the vaginal cuff while suturing. However, with the advent of laparoscopic hysterectomies, this final step has become technically challenging due to, among other things, limited visibility and access to the vaginal cuff for suturing.

SUMMARY

In accordance with an aspect of the present disclosure, a surgical device for closing a vaginal cuff is disclosed and includes a handle having an elongated shaft extending therefrom and a plurality of needles disposed within the elongated shaft and deployable from a distal end portion of the elongated shaft. Each of the plurality of needles includes a suture anchor at a distal end portion thereof, each suture anchor having a distal end of a suture engaged therewith with a free end extending therefrom. An anvil is disposed at a distal end of the elongated shaft and includes a plurality of apertures configured to receive the corresponding plurality of needles and suture anchors therethrough. A cutting mechanism is operably associated with the handle and is configured to cut tissue disposed relative to the elongated shaft upon actuation thereof. A firing mechanism is operably associated with the handle and is movable between an unactuated position wherein the plurality of needles and suture anchors remain retained within the elongated shaft, an actuated position wherein the plurality of needles and suture anchors deploy from the elongated shaft through the apertures in the anvil and into and through cervical tissue, and a reverted position wherein the plurality of needles retract through the cervical tissue, through the apertures in the anvil and back into the elongated shaft of the surgical device leaving the plurality of suture anchors and distal ends of the sutures engaged with the cervical tissue and the free ends of the plurality of sutures within view of the surgeon for tying off the vaginal cuff.

In aspects according to the present disclosure, the handle simultaneously deploys the plurality of needles and activates the cutting mechanism. In still other aspects according to the present disclosure, the plurality of sutures includes opposing pairs that are color coded or numbered to facilitate tying off the plurality of sutures.

In yet other aspects according to the present disclosure, the cutting mechanism includes an annular knife. In other aspects, the cutting mechanism is electrically activated to cut tissue. In still other aspects the anvil may be tilted or transitionable from a first position wherein the anvil is configured for insertion through the cervical os and a second position wherein the anvil is configured to clamp against the cervix.

In accordance with other aspects of the present disclosure, a method of closing a vaginal cuff is disclosed and includes inserting a surgical device having an anvil trans-cervically through a cervical os and clamping the anvil against the cervix while pushing the device cephalad to gain distance from critical anatomical structures. The method further includes firing a handle of the device to: deploy a plurality of needles having a complimentary plurality of suture anchors and sutures associated therewith into and through cervical tissue; and activate or extend a cutting mechanism to cut the cervix for removal. The method further includes releasing the handle to: retract the plurality of needles leaving the suture anchors and the distal ends of the sutures on the opposite side of the cervical tissue; and deactivate and or retract the cutting mechanism. The surgical device is then removed from the vaginal canal leaving the free ends of the sutures in situ within view of the surgeon, the uterus is removed through the vaginal canal and the plurality of sutures is tied off to close the vaginal cuff.

In aspects according to the present disclosure, the plurality of needles is deployed through the cervical tissue at an angle relative to the shaft of the device. In other aspects, the firing of the handle simultaneously deploys the plurality of needles and activates or extends the cutting mechanism. In other aspects, the method includes an initial step of incising the cervix os to facilitate insertion of the anvil of the surgical device therethrough.

In other aspects according to the present disclosure, the plurality of sutures is tied off in opposing pairs on opposite sides of the vaginal cuff. Each opposing pair may be color coded or numbered to facilitate tying off the plurality of sutures. In still other aspects, cutting mechanism includes an annular knife. In yet other aspects, the cutting mechanism may be electrically activated to cut tissue.

In accordance with an aspect of the present disclosure, a surgical device includes a handle having an elongated shaft extending therefrom that defines a longitudinal axis therethrough and has a distal end that is flared at an angle relative to the longitudinal axis. A plurality of needles is disposed within the elongated shaft and is deployable therefrom. Each of the plurality of needles includes a suture anchor at a distal end portion thereof. Each suture anchor has a distal end of a suture engaged therewith with a free end extending therefrom. An anvil is disposed at a distal end of the elongated shaft. The anvil is positionable through the cervical os and is selectively movable relative to the elongated shaft to clamp the anvil against the cervix. A cutting mechanism is operably associated with the handle and is configured to cut tissue disposed relative to the elongated shaft upon actuation or activation thereof.

A firing mechanism is operably associated with the handle and is movable between an unactuated position wherein the plurality of needles and suture anchors remain retained within the elongated shaft, an actuated position wherein the plurality of needles and suture anchors deploy from the elongated shaft at an angle relative to the elongated shaft into and through cervical tissue, and a reverted position wherein the plurality of needles retract through the cervical tissue back into the elongated shaft of the surgical device leaving the plurality of suture anchors and distal ends of the sutures engaged with the cervical tissue and the free ends of the plurality of sutures within the surgeons view for tying off the vaginal cuff.

In aspects according to the present disclosure, the handle is configured to simultaneously deploy the plurality of needles and activate or advance the cutting mechanism. In other aspects, the plurality of sutures includes opposing pairs that are color coded or numbered to facilitate tying off the plurality of sutures. In yet other aspects, the cutting mechanism includes an annular knife. In still other aspects, the cutting mechanism is electrically activated to cut tissue.

In aspects according to the present disclosure, the anvil is selectively transitionable between a first position to facilitate transition of the anvil through the cervical os and a second position to facilitate clamping of the anvil against the cervix.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein.

DETAILED DESCRIPTION

Embodiments of the present surgical devices used for closing a vaginal cuff are described in detail with reference to the drawings, in which like reference numerals designate identical or corresponding elements in each of the several views. As used herein, the term "distal" refers to that portion of structure farther from the user, while the term "proximal" refers to that portion of structure, closer to the user. As used herein, the term "clinician" refers to a doctor, nurse, or other care provider and may include support personnel.

In the following description, well-known functions or constructions are not described in detail to avoid obscuring the present disclosure in unnecessary detail.

Figure 1A:
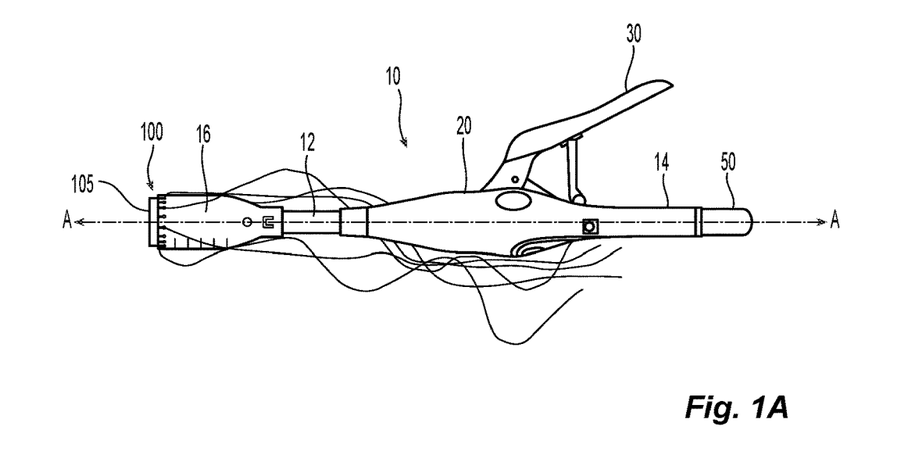
FIG. 1A is a side view of a surgical device for closing a vaginal cuff in accordance with the principles of the present disclosure.
Figure 1B:
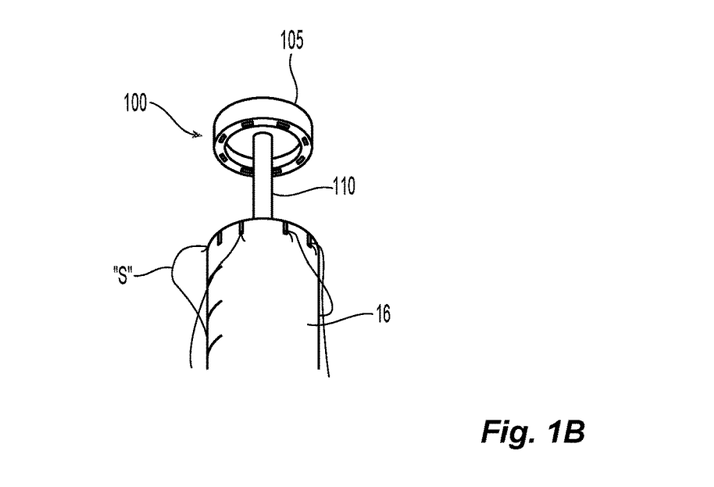
FIG. 1B is rear, perspective view of the surgical device of FIG. 1A.
Figure 1C:
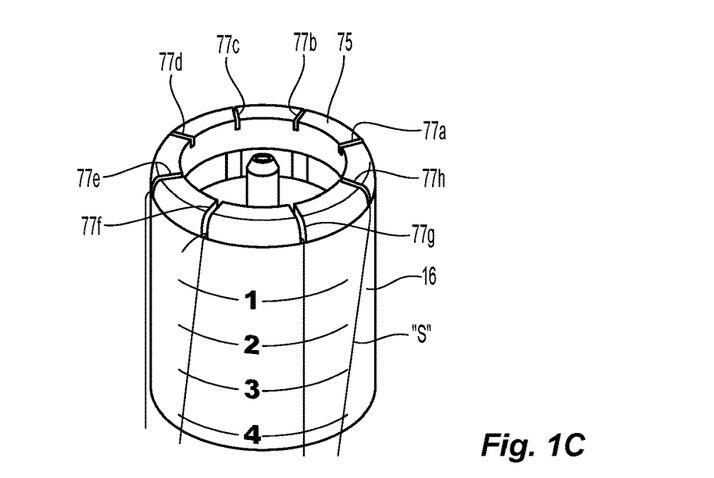
FIG. 1C is a top, perspective view of the surgical device of FIG. 1A.

Turning now to FIGS. 1A-1C, one embodiment of a surgical device for closing a vaginal cuff is shown, generally referred to as 10, is illustrated. Surgical device 10 defines a longitudinal axis "A-A" and includes a housing 20 having a shaft 12 that extends therefrom that supports a distal end portion 16. A handle 30 is operably coupled to the housing 20 and is selectively actuatable to fire the surgical device as described in more detail below. The distal end portion 16 supports an anvil assembly 100 at an end thereof that is selectively extendible via an anvil actuator 50 disposed at a proximal end portion 14 of housing 20 as described in more detail below.

Figure 1D:
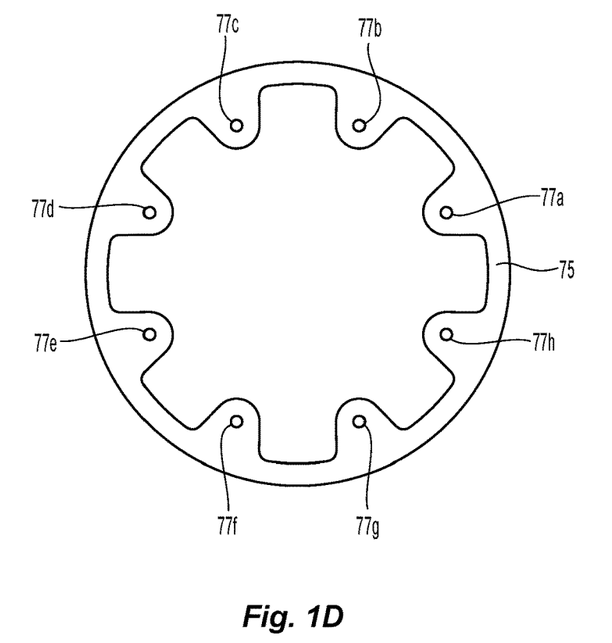
FIG. 1D is an enlarged, top view of a suture ring for use with the surgical device of FIG. 1A.

As best shown in FIGS. 1C and 1D, the anvil assembly 100 includes a suture ring 75 that includes a plurality of apertures 77a-77h defined therethrough that are configured to guide and retain a corresponding plurality of sutures "S" for tying off after the surgical device 10 is fired and removed. Apertures 77a-77h may include a geometry that allows the sutures "S" to be moved in a specific direction, e.g., off-axis A-A, to cinch the suture "S" in place against the ring 75.

Figure 1E:
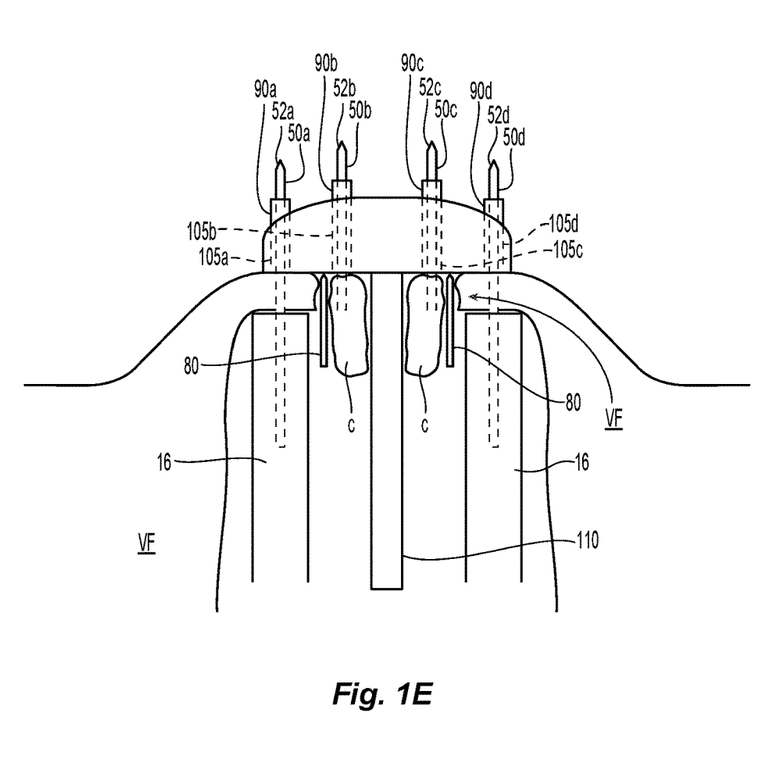
FIG. 1E is an enlarged, schematic view of a distal end portion of the surgical device of FIG. 1A shown in situ and in a deployed configuration.

As shown in FIGS. 1B and 1E, anvil actuator 50 is configured to selectively extend and retract an anvil 105 of the anvil assembly 100 for manipulation within the vaginal fornix "VF" and through the cervical os. More particularly, the anvil 105 is extended by actuating, e.g., rotating, the anvil actuator 50 to move the anvil 105 relative to the distal end portion 16 to facilitate insertion of the anvil 105 into and through the cervical os while maintaining the suture ring 75 within the vaginal fornix. "VF". As explained in more detail below, the anvil 105 is then retracted, e.g., by turning anvil actuator 50 in the opposite direction, against the cervical os to position the surgical device 10 for firing (See FIG. 1E).

The distal end portion 16 of surgical device 10 includes a plurality of needles 50a-50d retained therein that are configured for selective deployment from the distal end portion 16 upon actuation of the handle 30 to fire the surgical device 10. Each needle 50a-50d includes a sharpened point 52a-52d, respectively, at a distal end thereof configured to pierce tissue, e.g., the cervix, and a suture anchor 90a-90d, respectively, configured to anchor or retain a distal end of each suture "S" against the cervix.

The anvil 105 includes a plurality of channels 105a-105d defined therethrough configured to receive a corresponding plurality of needles 50a-50d and suture anchors 90a-90d therethrough upon deployment via actuation of handle 30 (See FIG. 1E). More particularly, when the handle 30 is actuated, e.g., squeezed toward housing 20, an annular pusher member 140 (See FIG. 4E) urges the needles 50a-50d distally through the suture ring 75, through the cervical tissue, and through the channels 105a-105d defined within the anvil 105 such that the distal ends 52a-52d of the needles and the suture anchors 90a-90d extend beyond the periphery of the anvil 105. A knife 80 is disposed within the distal end portion 16 of the surgical device 10 and is configured to extend into and cut the cervical tissue "C" upon actuation of the handle 30. In embodiments, the pusher member 140 is configured to simultaneously deploy the needles 50a-50d and extend the knife 80 upon actuation of the handle 30 (See FIG. 4E). The knife 80 may be annular or may be otherwise configured to cut the cervical tissue to create a vaginal cuff.

Once the needles 50a-50d and anchors 90a-90d are deployed and the knife cuts the vaginal cuff, the handle 30 is released resulting in the retraction of the needles 50a-50d back through the anvil 105 leaving the suture anchors 90*a*-90*d* beyond the periphery of the anvil 105. More particularly, the suture anchors 90*a*-90*d* are designed to disengage from the needles 50*a*-50*d* and reorient to a larger, obstructive profile preventing the suture anchors 90*a*-90*d* from reverting back through the channels 105*a*-105*d* (See FIGS. 4F and 4G). As a result, the suture anchors 90*a*-90*d* and the distal end of the sutures "S" remain on the opposing side of the cervix while the needles 50*a*-50*d* revert back into the distal end 16 of the surgical device. The suture ring 75, which during deployment of the needles 50*a*-50*d* remains within the vaginal fornix against the cervical tissue in opposition with the anvil 105, guides the sutures "S" during actuation and release of the handle 30 such that the free end of the sutures "S" remain in position around the suture ring 75 and within view of the surgeon.

Once the handle 30 is released and the needles 50*a*-50*d* are properly seated back within the distal end portion 16 of the surgical device 10, the surgical device 10 can be removed. As the surgical device 10 is being removed, the sutures "S" are released from the suture ring 75 allowing the free ends of the sutures "S" to remain within the vagina (or slightly extending out therefrom) and within view of the surgeon. The surgeon then removes the remaining uterine tissue through the vagina. Once all tissue is removed, the free ends of the sutures "S" are tied off in pairs to close the vaginal cuff. In embodiments, the sutures "S" may be color coded or numbered to facilitate pairing of the sutures "S" (See FIGS. 4I and 4J).

Figure 2:
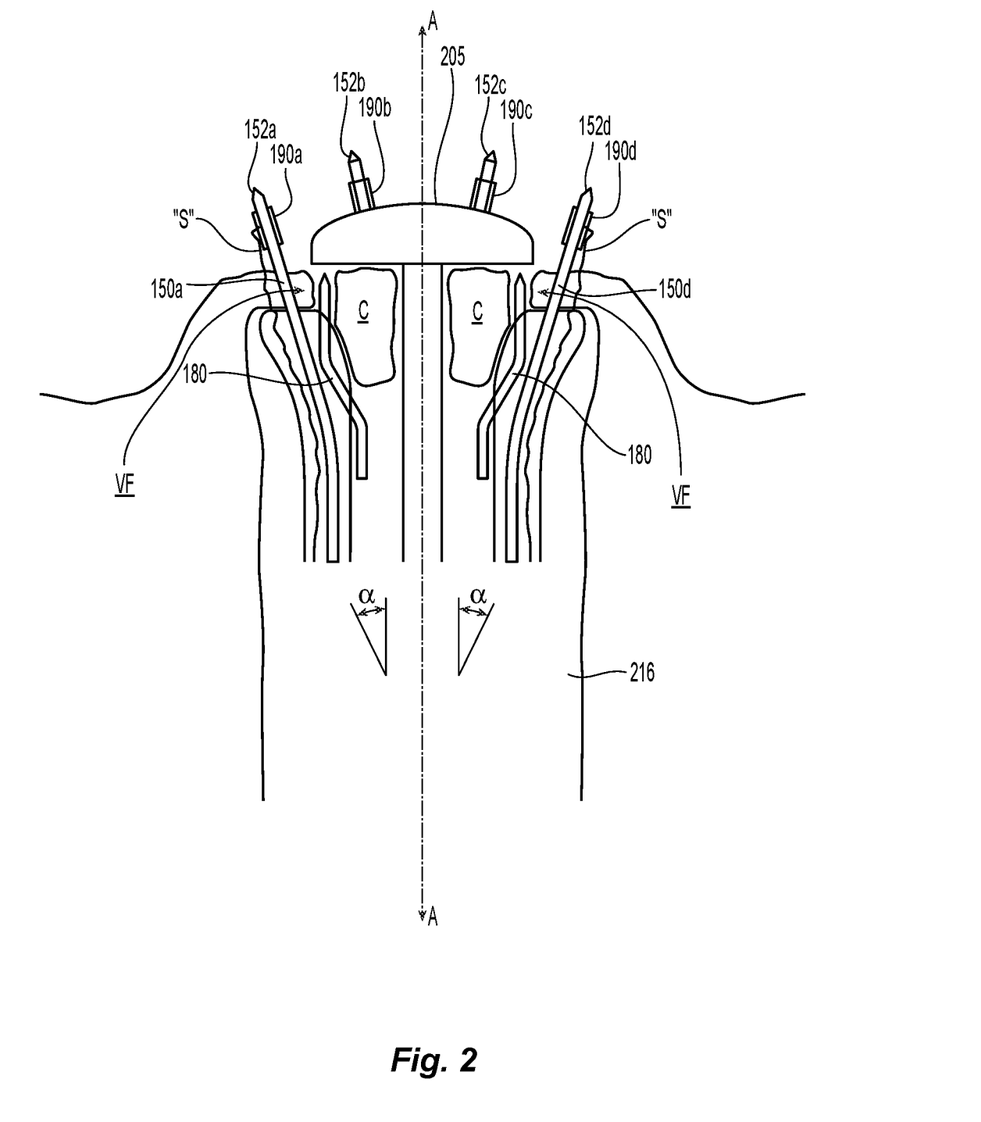
FIG. 2 is an enlarged, schematic view of a distal end portion of another embodiment of the surgical device of FIG. 1A in accordance with the principles of the present disclosure shown in situ and in a deployed configuration.

FIG. 2 shows another embodiment of a surgical device 200 according to the present disclosure that includes a flared distal end portion 216 to allow a larger annular margin of tissue to be captured when sutured. Surgical device 200 includes similar features to surgical device 10 and only those features that are different will be described herein.

As mentioned above the distal end portion 216 of surgical device 200 is angled or flared at an angle alpha ($\alpha$) relative to the longitudinal axis A-A. The needles 150*a*-150*d* are configured to deflect as the needles 150*a*-150*d* are deployed such that the needles 150*a*-150*d* engage the cervical tissue at substantially the same angle alpha ($\alpha$). This enables the annular array of needles 150*a*-150*d* to engage a wider margin of cervical tissue and eliminates the need for channels (See FIG. 1E) defined within the anvil 205, i.e., the needles 150*a*-150*d* are deployed in an annular array outside the periphery of the anvil 205. Surgical device 200 also includes a knife 180 that is selectively actuatable to cut the cervical tissue in a similar manner as described above. Knife 180 may be annular and simultaneously actuatable with the needles 150*a*-150*d*. Knife 180 may be angular or include angled features to facilitate deployment of the knife 180 through the flared distal end portion 216 of the surgical device 200.

When the surgical device 200 is fired, the needles 150*a*-150*d* and corresponding suture anchors 190*a*-190*d* pierce the cervical tissue and the knife 180 cuts an incision to create a vaginal cuff. When the handle 30 is released, the needles 150*a*-150*d* and the knife 180 retract to within the distal end portion 216 leaving the suture anchors 190*a*-190*d* on the opposing side of the cervical tissue with the free ends of the sutures "S" in the vagina. In a similar manner to that described above, the surgical device 200 is removed and the sutures "S" are tied off closing the vaginal cuff.

Figure 3:
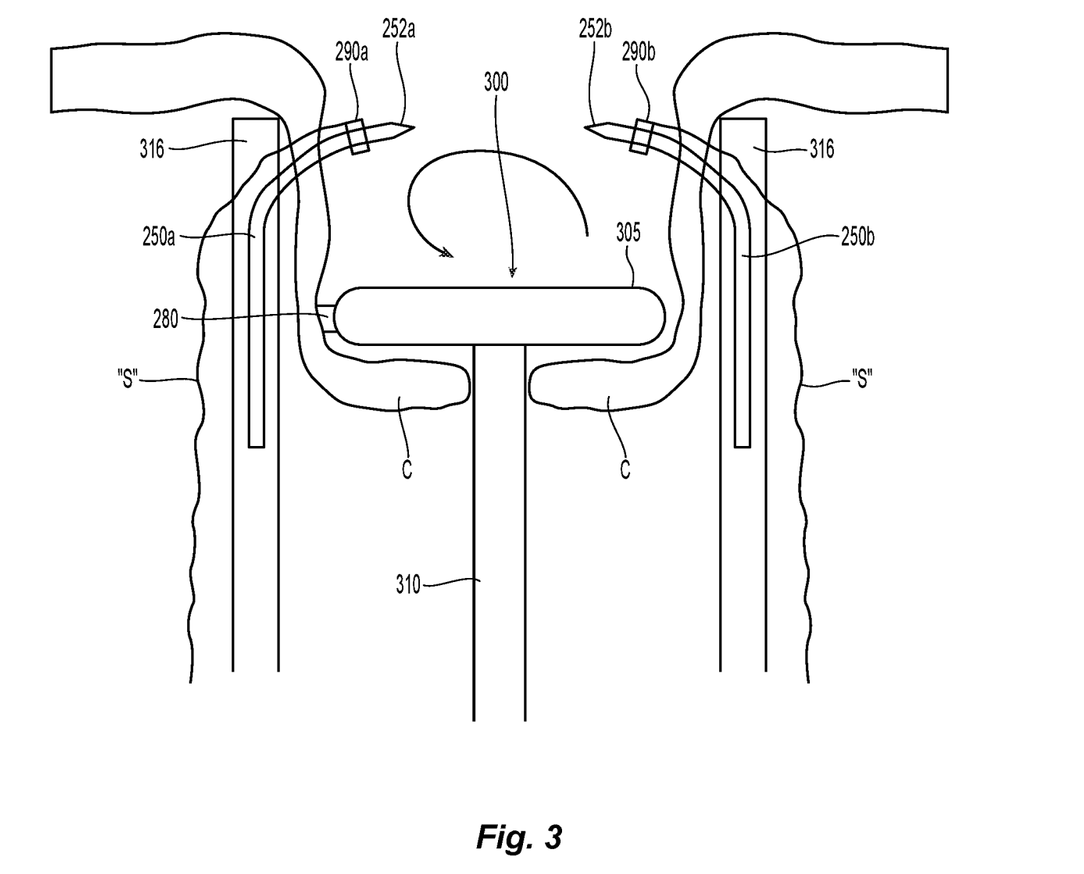
FIG. 3 is an enlarged, schematic view of a distal end portion of another embodiment of the surgical device of FIG. 1A in accordance with the principles of the present disclosure shown in situ and in a deployed configuration.

FIG. 3 shows another embodiment of a surgical device 300 according to the present disclosure that includes an annular distal end portion 316 including a cavity 317 defined therein that is configured to allow a larger annular margin of tissue to be captured when sutured. Surgical device 300 includes similar features to surgical devices 10, 200 and only those features that are different will be described herein.

As mentioned above the distal end portion 316 of surgical device 300 is annular in shape to define a cavity 317 therein for receiving cervical tissue. Surgical device 300 also includes an anvil 305 that is configured to pass through and into the cervix and that is manipulatable to engage cervical tissue on the opposing side thereof. The anvil 305 is then retracted against the cervical tissue, i.e., by rotating actuator 50 in an opposite direction, to position the cervical tissue within the cavity 317 and position the surgical device 300 for firing. A plurality of needles 250*a*-250*b* is disposed in the distal end portion 316 of the surgical device 300 and is configured to deploy proximate the distal most end of the distal end portion 316 at a position more interior to the anvil 305. This enables the needles 250*a*-250*b* to engage a wider margin of cervical tissue and eliminates the need for channels (See FIG. 1E) defined within the anvil 305, i.e., the needles 250*a*-250*b* and suture anchors 290*a*-290*b* are deployed more interior of the anvil 305. Surgical device 300 also includes a knife 280 that is selectively actuatable to cut the cervical tissue in a similar manner as described above. Knife 280 may be simultaneously actuatable with the needles 250*a*-250*b* and suture anchors 290*a*-290*b*. Knife 280 may be configured to rotate around the periphery of the anvil 305 to cut an incision in the cervix to create a vaginal cuff when the handle 30 is actuated.

When the surgical device 300 is fired, the needles 250*a*-250*b* and corresponding suture anchors 290*a*-290*b* pierce the cervical tissue and the knife 280 cuts an incision to create a vaginal cuff. When the handle 30 is released, the needles 250*a*-250*b* and the knife 280 retract to within the distal end portion 316 and the anvil 305, respectively, leaving the suture anchors 290*a*-290*b* on the opposing side of the cervical tissue with the free ends of the sutures "S" in the vagina within view of the surgeon. In a similar manner to that described above, the surgical device 300 is removed and the sutures "S" are tied off closing the vaginal cuff.

Figure 4A:
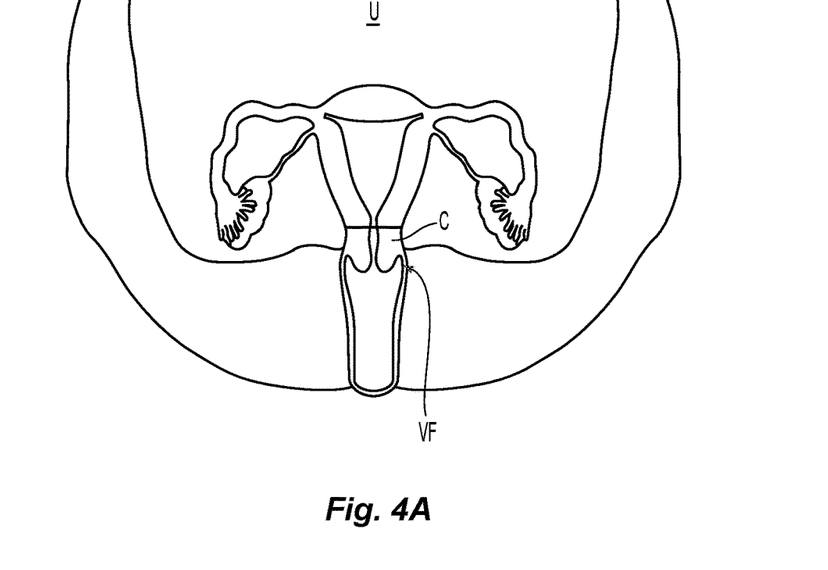
FIG. 4A-4J are schematic views showing a method for performing a colpotomy and closing a vaginal cuff according to the principles of the present disclosure.
Figure 4B:
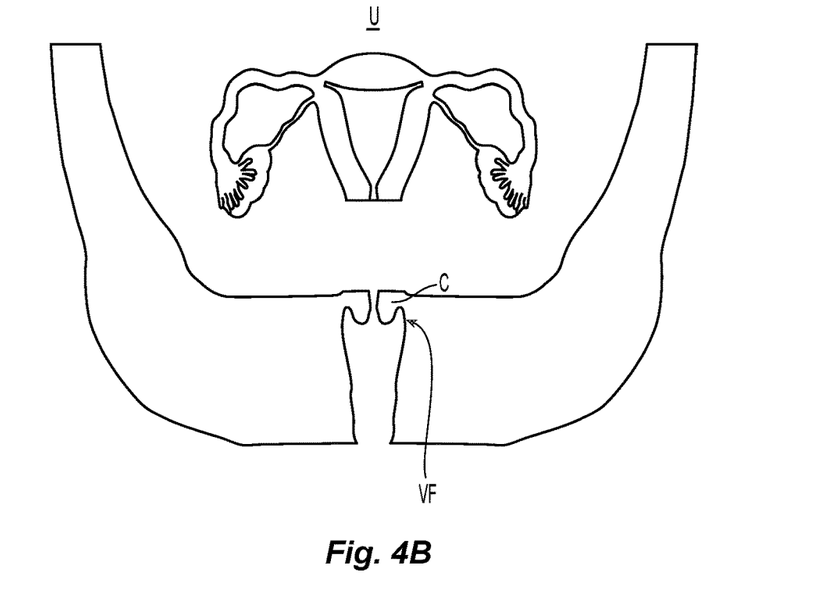
Figure 4C:
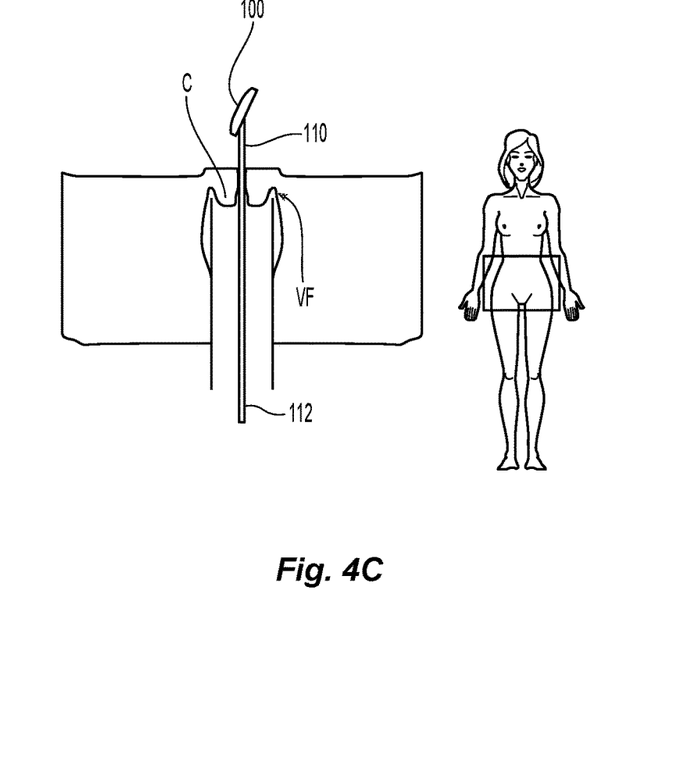
Figure 4D:
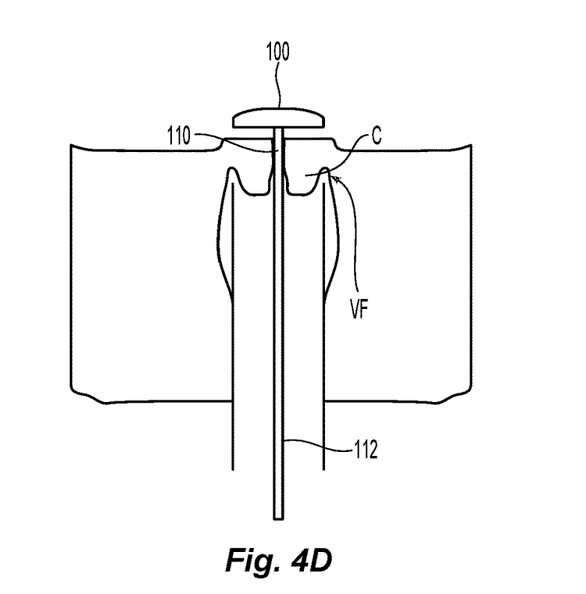
Figure 4E:
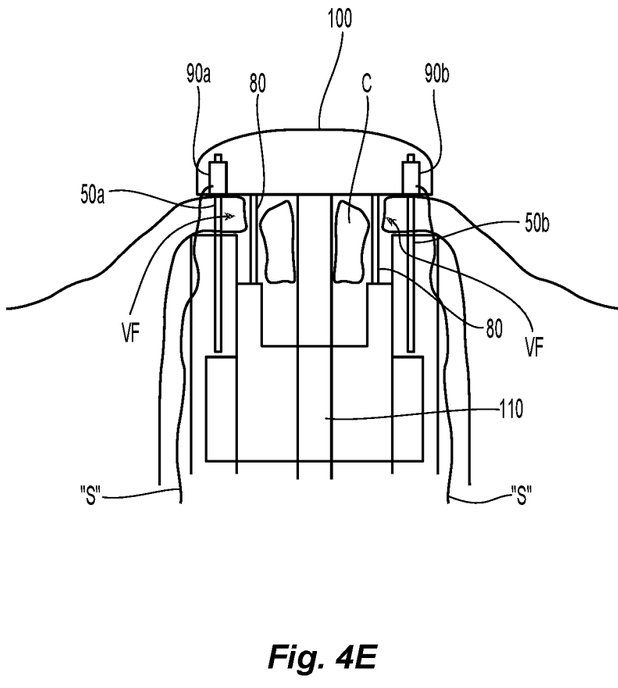
Figure 4F:
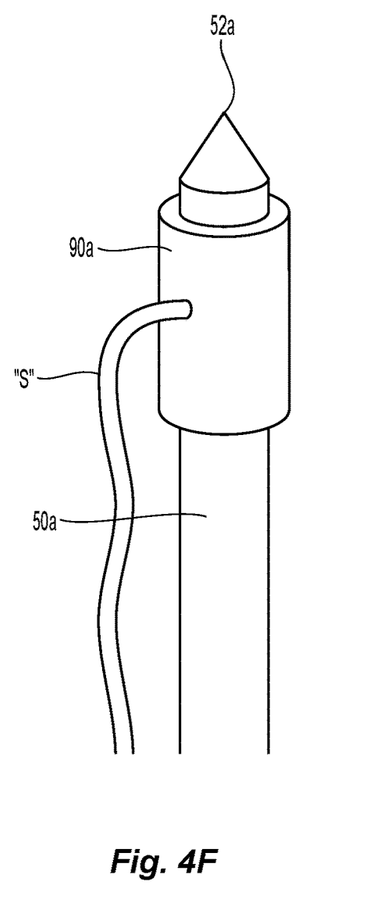
Figure 4G:
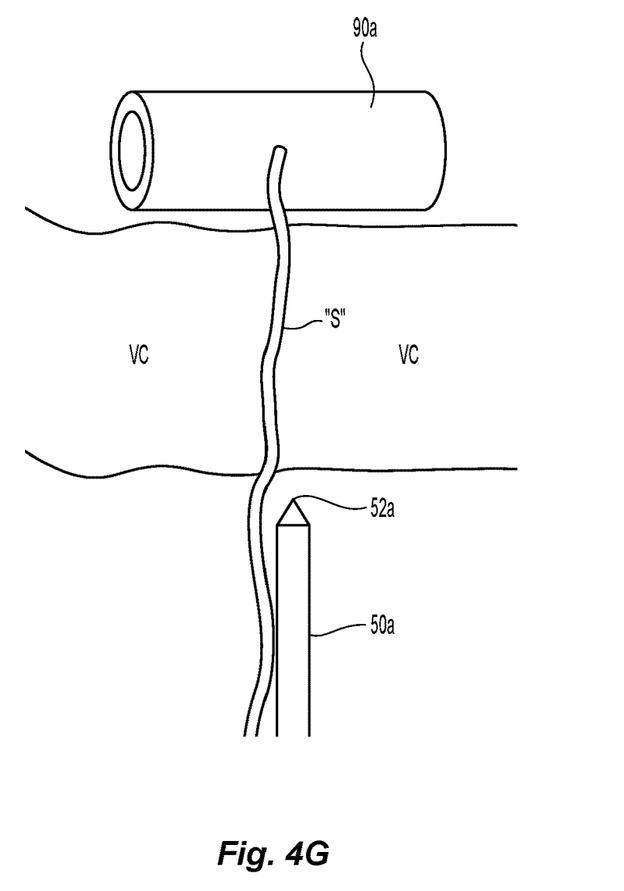

FIGS. 4A-4J show a method according to the present disclosure for closing the vaginal cuff and includes an initial step of excising the uterus from the cervix and making an incision therein sized to receive a surgical device, e.g., surgical device 10, having an anvil 105 at a distal end portion 16 thereof (FIGS. 4A-4B). The method further includes inserting the anvil 105 trans-cervically through the cervical os and clamping the anvil 105 against the cervix while pushing the device 10 cephalad to gain distance from critical anatomical structures (FIGS. 4C-4D). As mentioned above, the anvil 105 may be tilted to facilitate insertion through the cervical os.

Figure 4H:
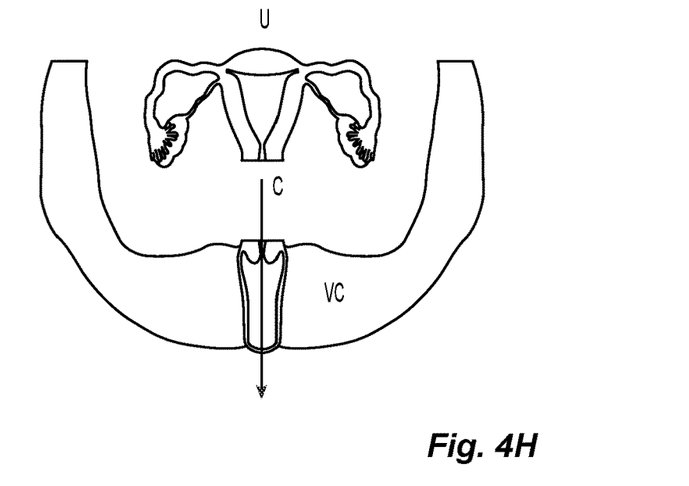

The method further includes firing a handle 30 of the device 10 to: deploy a plurality of needles 50*a*-50*b* having a complimentary plurality of suture anchors 90*a*-90*b* and sutures "S" associated therewith into and through the cervical tissue; and activate a cutting mechanism 80 to cut the cervix for removal. The method further includes releasing the handle 30 to: retract the plurality of needles 50*a*-50*b* leaving the suture anchors 90*a*-90*b* and the distal ends of the sutures "S" on the opposite side of the cervical tissue (FIGS. 4F-4G); and deactivate and/or retract the cutting mechanism 80. The surgical device 10 is then removed from the vaginal canal leaving the free ends of the sutures "S" in the vagina within view of the surgeon (or extending out therefrom. The uterus is removed through the vaginal canal (FIG. 4H) and the plurality of sutures "S" is tied off to close the vaginal cuff "VC" (FIGS. 4I-4J).

In aspects according to the present disclosure, the plurality of needles, e.g., needles 150a-150b, is deployed through the cervical tissue at an angle relative to the shaft of the surgical device 200. In other aspects, the firing of the handle 30 simultaneously deploys the plurality of needles 50a-50b and activates the cutting mechanism 80. In other aspects, the method includes an initial step of incising the cervix os to facilitate insertion of the anvil 105 of the surgical device 10 therethrough.

Figure 4I:
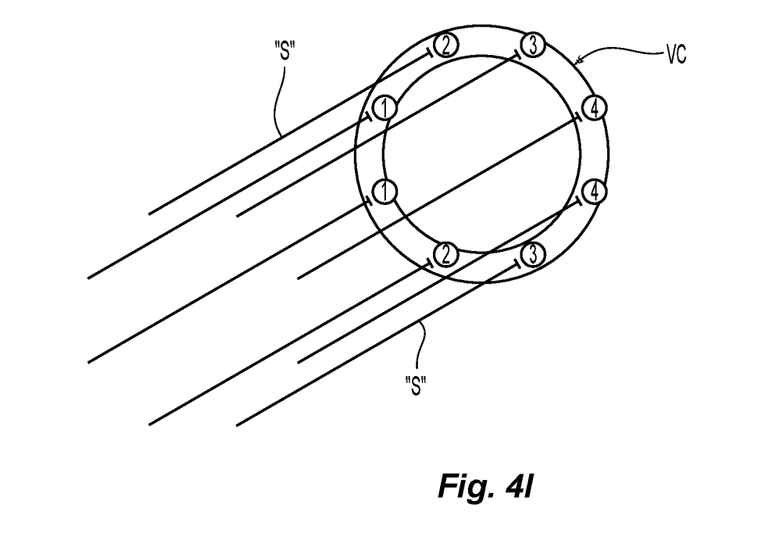
Figure 4J:
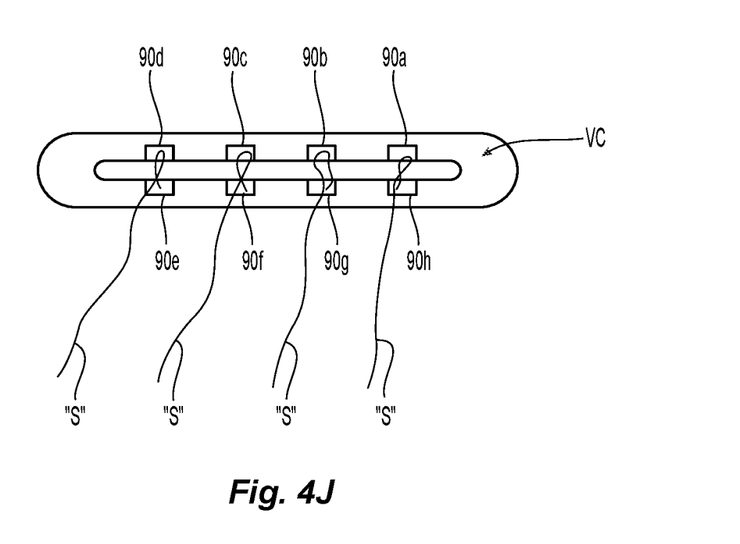

In other aspects according to the present disclosure, the plurality of sutures "S" is tied off in opposing pairs on opposite sides of the vaginal cuff (FIGS. 4I-4J). Each opposing pair may be color coded or numbered to facilitate tying off the plurality of sutures "S". In still other aspects, cutting mechanism 80 includes an annular knife. In yet other aspects, the cutting mechanism 80 may be electrically activated to cut tissue.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416, and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical device for closing a vaginal cuff, comprising:
   a body;
   a plurality of suture anchors disposed within the body and deployable from the body, each suture anchor of the plurality of suture anchors engaging a first end portion of a suture;
   an anvil operably positioned relative to a distal end of the body to enable receipt of cervical tissue between the anvil and the body, the anvil defining a distal-most extent;
   a cutting mechanism configured to cut the cervical tissue disposed between the distal end of the body and the anvil; and
   an actuator operably coupled to the plurality of suture anchors and configured to drive the plurality of suture anchors from an un-actuated position, wherein the plurality of suture anchors are retained within the body, to an actuated position, wherein the plurality of suture anchors are deployed from the body, through the cervical tissue, and through or around the anvil to a position distal of the distal-most extent of the anvil, thereby deploying the first end portions of the sutures from the body, through the cervical tissue, and through or around the anvil to a position distal of the distal-most extent of the anvil with the sutures extending from the first end portions thereof, through the cervical tissue, to second end portions thereof that define free ends to enable tying off of the sutures to close the cervical tissue, thereby closing a vaginal cuff.

2. The surgical device according to claim 1, wherein the actuator is configured to simultaneously deploy the plurality of suture anchors and to activate the cutting mechanism to cut the cervical tissue.

3. The surgical device according to claim 1, wherein the plurality of sutures includes opposing pairs that are color coded or numbered to facilitate tying off of the sutures.

4. The surgical device according to claim 1, wherein the cutting mechanism includes an annular knife that is selectively deployable between the body and the anvil.

5. The surgical device according to claim 1, wherein the cutting mechanism is electrically energized to cut the cervical tissue.

6. The surgical device according to claim 1, wherein the actuator is operably coupled to a handle associated with the body.

7. The surgical device according to claim 6, wherein the handle is manually actuatable.

8. The surgical device according to claim 1, wherein the an anvil is retractable into the distal end of the body.

9. The surgical device according to claim 1, further comprising a plurality of needles, each needle operably coupled to one of the suture anchor, and wherein the needles are deployed from the body, through the cervical tissue, and through or around the anvil to a position distal of the distal-most extent of the anvil, thereby deploying the suture holders and the first end portions of the sutures from the body, through the cervical tissue, and through or around the anvil to the position distal of the distal-most extent of the anvil.

10. The surgical device according to claim 9, wherein the needles are operably coupled to the actuator and wherein the actuator is further actuatable to retract the needles proximally into the body while leaving the suture holders and the first and portions of the sutures behind.

11. The surgical device according to claim 1, wherein the plurality of suture anchors are driven from the un-actuated position to the actuated position through apertures defined in the anvil to the position distal of the distal-most extent of the anvil.

12. The surgical device according to claim 1, wherein the plurality of suture anchors are driven from the un-actuated position to the actuated position annularly about an outer circumference of the anvil to the position distal of the distal-most extent of the anvil.

13. The surgical device according to claim 12, wherein the plurality of suture anchors are driven at radially-outward angles relative to a longitudinal axis of the body.

14. The surgical device according to claim 1, wherein the plurality of suture anchors are driven from the un-actuated position to the actuated position radially-inwardly towards one another.

15. The surgical device according to claim 1, wherein the body is at least a portion of an elongated shaft.

16. The surgical device according to claim 1, wherein the body is a radially-flared distal portion of the elongated shaft.

17. The device according to claim 1, wherein the anvil is longitudinally movable relative to the body to clamp the cervical tissue between anvil and the distal end of the body.

* * * * *